US008871239B2

(12) United States Patent
Zhao

(10) Patent No.: US 8,871,239 B2
(45) Date of Patent: Oct. 28, 2014

(54) POLYMERIC MATERIALS FOR MEDICAL DEVICES

(75) Inventor: Jonathon Z. Zhao, Belle Meade, NJ (US)

(73) Assignee: Cordis Corporation

( * ) Notice: Subject to any disclaimer, the term of this patent is extended or adjusted under 35 U.S.C. 154(b) by 0 days.

(21) Appl. No.: 13/544,043

(22) Filed: Jul. 9, 2012

(65) Prior Publication Data

US 2012/0276172 A1 Nov. 1, 2012

Related U.S. Application Data

(63) Continuation of application No. 11/939,805, filed on Nov. 14, 2007, now Pat. No. 8,216,600.

(51) Int. Cl.
| | |
|---|---|
| *A61K 9/00* | (2006.01) |
| *A61P 7/02* | (2006.01) |
| *A61P 29/00* | (2006.01) |
| *A61L 29/08* | (2006.01) |
| *A61L 31/16* | (2006.01) |
| *A61L 29/04* | (2006.01) |
| *A61L 27/16* | (2006.01) |
| *A61L 29/16* | (2006.01) |
| *A61L 31/10* | (2006.01) |
| *A61L 31/04* | (2006.01) |
| *A61L 27/34* | (2006.01) |
| *A61L 27/54* | (2006.01) |

(52) U.S. Cl.
CPC ............... *A61L 29/085* (2013.01); *A61L 31/16* (2013.01); *A61L 29/041* (2013.01); *A61L 27/16* (2013.01); *A61L 29/16* (2013.01); *A61L 2300/41* (2013.01); *A61L 2300/416* (2013.01); *A61L 31/10* (2013.01); *A61L 2300/42* (2013.01); *A61L 31/048* (2013.01); *A61L 27/34* (2013.01); *A61L 27/54* (2013.01)
USPC ......................................... 424/423; 424/400

(58) Field of Classification Search
None
See application file for complete search history.

(56) References Cited

U.S. PATENT DOCUMENTS

| | | | | |
|---|---|---|---|---|
| 4,487,882 | A | * | 12/1984 | Ueta et al. ...................... 524/505 |
| 4,733,665 | A | | 3/1988 | Palmaz |
| 4,800,882 | A | | 1/1989 | Gianturco |
| 4,886,062 | A | | 12/1989 | Wiktor |
| 5,514,154 | A | | 5/1996 | Lau et al. |
| 6,110,483 | A | | 8/2000 | Whitbourne et al. |
| 6,153,252 | A | | 11/2000 | Hossainy et al. |
| 6,190,403 | B1 | | 2/2001 | Fischell et al. |
| 6,746,773 | B2 | | 6/2004 | Llanos et al. |
| 7,070,616 | B2 | * | 7/2006 | Majercak et al. ............ 623/1.24 |
| 7,261,946 | B2 | | 8/2007 | Claude |
| 8,034,874 | B2 | * | 10/2011 | Strickler et al. ................ 525/88 |
| 8,216,600 | B2 | | 7/2012 | Zhao |
| 2002/0051730 | A1 | | 5/2002 | Bodnar et al. |
| 2004/0171765 | A1 | | 9/2004 | Tsuji et al. |
| 2005/0107531 | A1 | | 5/2005 | Claude |
| 2006/0047095 | A1 | * | 3/2006 | Pacetti .......................... 526/242 |
| 2006/0200229 | A1 | | 9/2006 | Burgermeister et al. |
| 2007/0082393 | A1 | * | 4/2007 | Lodhi et al. ................... 435/325 |
| 2007/0178133 | A1 | * | 8/2007 | Rolland ......................... 424/423 |
| 2007/0259101 | A1 | | 11/2007 | Kleiner et al. |

FOREIGN PATENT DOCUMENTS

| | | | |
|---|---|---|---|
| EP | 1566187 | A2 | 5/2003 |
| EP | 1566187 | A3 | 5/2003 |
| JP | 2007514808 | | 7/2006 |
| WO | WO9955396 | A | 11/1999 |
| WO | WO0187372 | A | 11/2001 |
| WO | WO03022324 | A | 3/2003 |
| WO | WO03045582 | A | 6/2003 |
| WO | WO03082368 | A | 10/2003 |
| WO | 2006026521 | | 3/2006 |
| WO | WO 2008064058 | * | 5/2008 |

OTHER PUBLICATIONS

Gelin et al. "Synthesis of an original poly(vinylidene fluoride-co-hexafluoropropylene)-g-perfluoropolyether graft copolymer" Journal of Fluorine Chemistry vol. 119, Issue 1, Jan 2003. pp. 53-58.*
Notification of Reasons for Refusal in corresponding Japanese Application No. 2008-291084 dated Apr. 30, 2013.
Ajroldi, G., et al., "Fluoroelastomers-Dependence of Relaxation Phenomena on Composition," Polymer, Dec. 1989, vol. 30, pp. 2180-.
Hanson, et al., "Interruption of Acute Platelet-Dependent Thrombosis by the Synthetic Antithrombin D-phenylalanyl-L-prolylL-Arginyl Chloromethyl Ketone," Proc. Natl. Acad. Sci. USA, Medicl Sciences, May 1988, vol. 85, pp. 3184-3188.
European Search Report, Feb. 24, 2009 for corresponding EP Patent Application No. EP08169016.
European Search Opinion, Feb. 24, 2009 for corresponding EP Patent Application No. EP08169016.
European Search Report Jul. 6, 2005 for corresponding EP Patent Application No. EP05011307.

* cited by examiner

*Primary Examiner* — Robert A Wax
*Assistant Examiner* — Danah Al-Awadi

(57) ABSTRACT

The present invention includes biocompatible polymeric coatings, membranes, matrices, and films to be used with implantable medical devices. Medical devices containing such materials applied to a surface thereof contain a film-forming fluorous homo-polymer or copolymer containing the polymerized residue of a fluorous moiety, wherein the relative amounts of the polymerized residues of one or more moieties are effective to provide the coating and films with properties effective for use in coating implantable med devices.

6 Claims, 5 Drawing Sheets

POLYMERIC MATERIALS FOR MEDICAL DEVICES

CROSS-REFERENCE TO RELATED APPLICATIONS

This application is a continuation of U.S. patent application Ser. No. 11/939,805, filed Nov. 14, 2007, now U.S. Pat. No. 8,216,600, the entire contents of which are incorporated herein by reference.

FIELD OF THE INVENTION

The invention relates to the use of fluorous homo or co-polymers as coatings and matrices for implantable medical devices. In particular, this invention relates to a fluorous homo or co-polymer employed as a carrier matrix for a therapeutic agent such that the agent may be delivered locally and in a sustained fashion when the polymer having the agent therein is applied to an implantable medical device.

BACKGROUND OF THE INVENTION

Implantable medical devices are employed to restore the normal function of the human body. For example, some devices are placed within a conduit located within the human body to restore the patency of the conduit. Other devices serve orthopedic functions such as replacing or repairing joints or bones. These devices include, without limitation, stents, catheters, sutures, meshes, vascular grafts, shunts, filters for removing emboli, artificial hips and bone anchors. Stents are generally a mesh tubular structure that is placed within a vessel. Stents are percutaneously placed within the vessel whereby the stent has a first compressed shape for passage through the vasculature of the patient to a targeted area where it is necessary to restore the patency of the vessel. Once at the targeted area the stent is expanded into a second shape, usually after the area has already been subject to a procedure, such as angioplasty, that opens the lumen of the vessel. Once the stent is expanded the lumen of the vessel is remodeled restoring adequate blood flow through the vessel.

A stent located within a vessel often stimulates reactions that result in the formation of clots (thrombosis) or smooth muscle tissue proliferation (restenosis) that causes the lumen to constrict. In order to avoid these complications, a variety of stent coatings and compositions have been proposed that limit adverse reactions. For example, certain coatings reduce the stimulus the stent provides to the injured lumen wall, thus reducing the tendency towards thrombosis or restenosis. Alternately, the coating may deliver a pharmaceutical/therapeutic agent or drug to the lumen that reduces restenosis. Typically, the therapeutic agent is embedded within the matrix of a polymer coating that is applied to the stent. The agent is delivered via diffusion through a bulk polymer, through pores that are created in the polymer structure, or by erosion of a biodegradable coating. It is necessary to ensure that the proper amount of agent is delivered to the targeted area. In order to deliver the therapeutic agent in a predictable manner it is necessary to ensure that a polymer will permit proper elution.

Both bioabsorbable and biostable polymeric compositions have been used as coatings for stents that will provide a stable platform for the predictable delivery of a therapeutic agent. These are generally polymeric coatings that either encapsulate a pharmaceutical/therapeutic agent or drug, e.g. taxol, rapamycin, etc., or bind such an agent to the surface, e.g. heparin-coated stents. These coatings are applied to the stent in a number of ways, including, though not limited to, dip, spray, or spin coating processes. One class of biostable materials that has been reported as coatings for stents is fluorous homopolymers. Polytetrafluoroethylene (PTFE) homopolymers. These homopolymers, however, are not soluble in any solvent at reasonable temperatures and therefore are difficult to coat onto small medical devices while maintaining important features of the devices (e.g. slots in stents).

Another approach has been to employ coatings made from poly(vinylidene flouride) homopolymers and containing pharmaceutical/therapeutic agents or drugs for release have been suggested. Like most crystalline fluorous homopolymers, however, these are difficult to apply as high quality films onto surfaces without subjecting them to relatively high temperatures, e.g. greater than about 125-200° C., that correspond to the melting temperature of the polymer.

One approach to providing a more stable platform is disclosed in U.S. Pat. No. 6,746,773—Llanos that discloses methods and composition for biocompatible coatings and films. These coatings are used on implantable medical devices and medical devices comprising such coatings and films applied to a surface thereof that is to be in contact with body tissue of a mammal. The biocompatible film provides an inert surface to be in contact with body tissue of a mammal upon implantation of the device in the mammal. The coating and film comprise a film-forming fluorous copolymer comprising the polymerized residue of a first moiety selected from the group consisting of vinylidene fluoride (VDF) and hexafluoropropylene (HFP).

It would be advantageous to develop additional fluorous coatings for implantable medical devices that offer a wider range of hydrophobicity and better mechanical properties. This will allow the coating to reduce thrombosis, restenosis, or other adverse reactions, that may include, but do not require, the use of pharmaceutical or therapeutic agents or drugs to achieve such affects. The coating will also possess physical and mechanical properties effective for use at relatively low maximum temperatures. It would also be advantageous to develop additional fluorous coatings with various physical properties to meet delivery parameters of a wide-range of pharmaceutical agents.

SUMMARY OF THE INVENTION

Fluorous based biocompatible coatings and films for use on implantable medical devices are provided. The biocompatible film of the present invention is applied to an implantable medical device and provides an inert surface that will be in contact with body tissue of a mammal upon implantation of the device. The coating and film comprises a film-forming polymerized residue of one or more fluorous monomers in varying molar ratios. Fluorous polymers are typically hydrophobic and biocompatible and are suitable for use within a conduit of a human body such as a blood vessel.

The copolymers employed in the coating have varying physical and chemical properties depending on the monomers used and the respective ratios between them. The final physical properties may also be affected to a lesser degree by the end groups of the copolymers. Commonly used monomers include perfluoroether (PFE), fluorous acrylates, VDF, HFP, tetrafluoroethylene (TFE). Alternatively, the various fluorous polymers are mixed together to form blends that have varying physical properties.

In certain instances it is desirable to remove an implantable device from the body after a certain time. The present invention provides an inert, low surface energy coating for implantable medical devices that are later retrieved. For example, the low surface energy coating makes wetting of the device surface and protein deposition thereon difficult which could decrease the formation of thrombus on the implant, leading to better performance of an implantable device such as a stent.

The coatings may comprise pharmaceutical or therapeutic agents in amounts effective for achieving a desired therapeutic result. For example thrombosis or restenosis may be reduced through the release of agents that the coating controls. Films prepared from the fluorous copolymer or polymer blend coatings of the present invention provide the physical and mechanical properties required of conventional coated medical devices, even where maximum temperatures to which the device, coatings and films are exposed are limited to relatively low temperatures, e.g. less than about 100° C., preferably at about ambient temperatures. This is particularly important when using the coating/film to deliver pharmaceutical/therapeutic agent or drugs that are heat sensitive, or when applying the coating onto temperature-sensitive devices such as, but not limited to, catheters.

Therapeutic agents possess a wide range of physical and chemical properties. These agents are expected to provide various functions to address one or more conditions such as inflammation, neointimal growth or thrombus that alone, or in combination, may occur after an implant is placed. Polymers of varying properties are used to maximize the therapeutic potential of each of these agents. For example, a hydrophilic agent may require a substantially hydrophobic polymer layer to slow the release of the agent from the polymer matrix of the coating. Addition of a third component to an established perfluorous copolymer P(VDF-co-HFP) may provide such required flexibility of the polymer. For instance, the addition of vinyl acetate or a styrene component to P(VDF-co-HFP), thereby producing P(VDF-co-HFP-co-vinyl acetate) or P(VDF-co-HFP-co-styrene), respectively, will likely strengthen the coating matrix and likely result in a prolonged release of an agent from the drug/polymer matrix. The molar ratio of the combined residues of VDF and FIFP to the vinyl acetate can be in a range from 0.95:0.05 to 0.1:0.9.

DETAILED DESCRIPTION OF THE INVENTION

Figure 1:
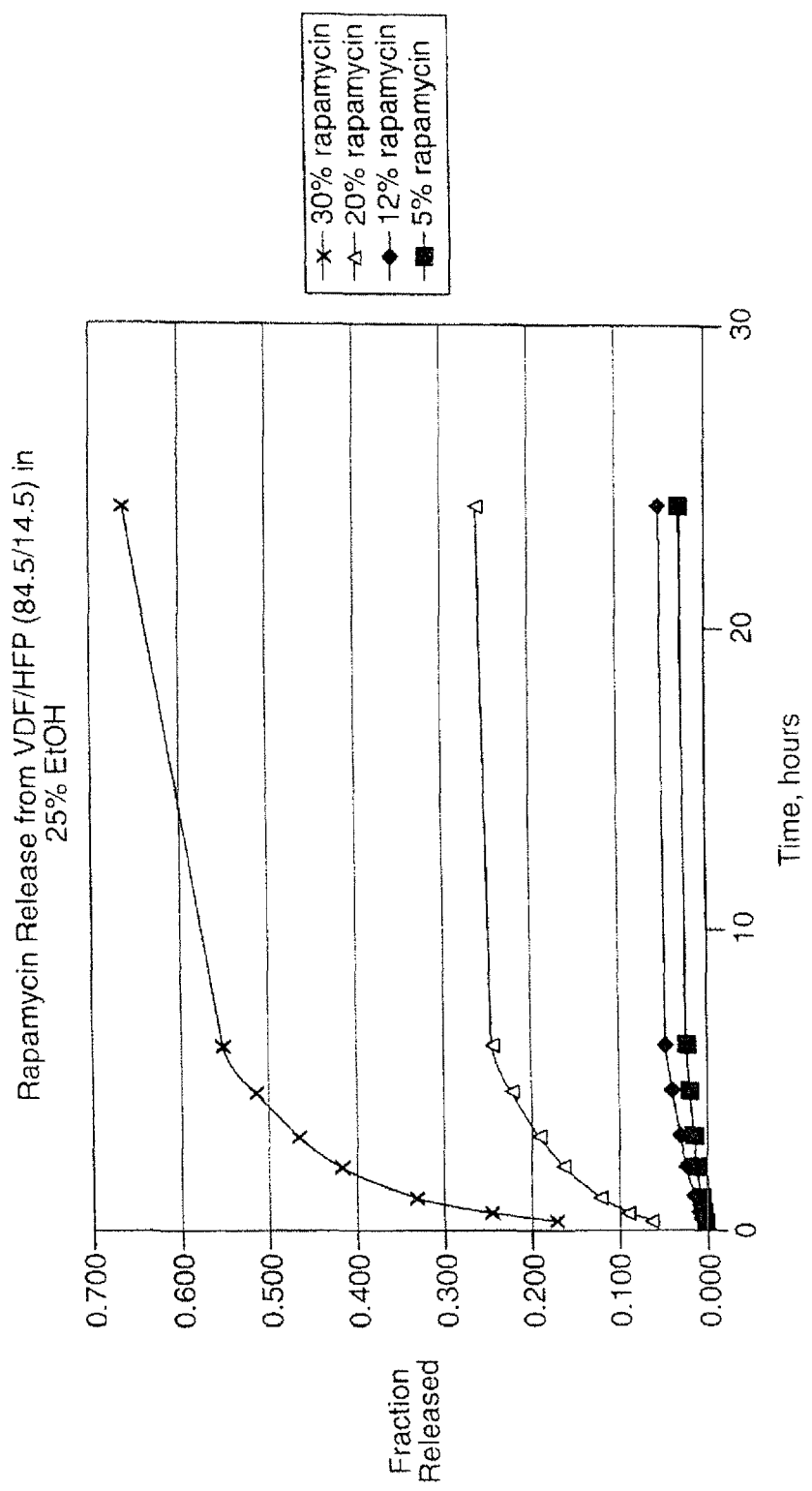
FIG. 1 illustrates the fraction of drug released as a function of time from coatings of the present invention over which no topcoat has been disposed.

The present invention provides polymeric coatings comprising a fluorous copolymer that may be applied to an implantable medical device such as a stents or orthopedic implant. The device will be coated with a film of the fluorous polymeric material in an amount effective to reduce thrombosis and/or restenosis when the device is implanted within a conduit of a human.

As used herein, fluorous copolymers means those copolymers comprising the polymerized residue selected from the group consisting of vinylidene fluoride (VDF), perfluoropolyethers (PFPE), and tetrafluoroethylene (TFE), perfluorous acrylate (PFL), hexafluoropropylene (HFP) among others. The molar ratios of these monomers may be adjusted such that the final copolymers may be most optimal as a drug delivery matrix associated with a medical device with a desirable toughness or elastomeric properties effective for use in coating implantable medical devices.

The present invention comprises fluorous copolymers and polymer blends that provide improved biocompatible coatings for medical devices. These coatings provide inert surfaces that reduce thrombosis, restenosis, and other undesirable reactions. While most reported coatings made from fluorous homopolymers such as PTFE are insoluble in regular organic solvent such as tetrahydrofuran (THF), and/or require high heat, e.g. greater than about 125° C., to obtain films with adequate physical and mechanical properties for use on implantable devices, e.g. stents, or are not particularly tough or elastomeric, films prepared from fluorous copolymer and polymer blend coatings of the present invention provide adequate adhesion, toughness or elasticity, and resistance to cracking when formed on medical devices claimed herein. In certain embodiments, this is the case even where the coated devices are subjected to relatively low maximum temperatures, e.g. less than about 100° C., preferably less than about 60° C., and more preferably about 40° C. or less.

The fluorous copolymers and polymer blends used as drug delivery matrices or coatings according to the present invention are polymers that have molecular weight high enough so as not to be waxy or tacky. The polymers and films formed therefrom adhere to the stent and are not readily deformable after deposition on the stent preventing them from being displaced by hemodynamic stresses. The polymer molecular weight provides sufficient toughness so that the polymer coating will not be rubbed off during handling or deployment of the device. In certain embodiments the coating will not crack during expansion of a device during deployment in a conduit.

Coatings of the present invention comprise fluorous copolymers, as defined hereinabove. The first, second, and third moiety copolymerized with the first moiety to prepare the fluorous copolymer may be selected from those biocompatible monomers that would provide biocompatible polymers acceptable for implantation in a mammal, while maintaining sufficient elastomeric film properties for use on medical devices claimed herein. Such monomers include, without limitation, hexafluoropropylene (HFP), tetrafluoroethylene (TFE), vinylidene fluoride (VDF), perfluoropolyethers (PFPE), and tetrafluoroethylene (TFE), perfluorous acrylate (PFL), hexafluoropropylene (HFP) and hexafluoroisobutylene. Each of these monomers will bring a unique set of desirable properties to the final copolymer. For instance, perfluoroether is inert, transparent, and chemical and thermally stable. Depending on the needs as a coating for medical devices, AB or ABA type copolymers may be created from the above monomers to tailor the physical and chemical properties of the final copolymers or blends. The ratios of the monomers should also be tailored so that the fluorous copolymers and blends are soluble, in varying degrees, in solvents such as dimethylacetamide (DMAc), tetrahydrofuran, dimethyl formamide, dimethyl sulfoxide and n-methylpyrrolidone for easy processing. Some are soluble in methylethylketone (MEK), acetone, methanol and other solvents commonly used in applying coatings to conventional implantable medical devices.

Conventional fluorous homopolymers are crystalline and difficult to apply as high quality films onto metal surfaces without exposing the coatings to relatively high temperatures that correspond to the melting temperature (Tm) of the polymer. The elevated temperature serves to provide films prepared from such PVDF homopolymer coatings that exhibit sufficient adhesion of the film to the device, while preferably maintaining sufficient flexibility to resist film cracking upon expansion/contraction of the coated medical device. Certain films and coatings according to the present invention provide these same physical and mechanical properties, or essentially the same properties, even when the maximum temperatures to which the coatings and films are exposed is less than about 100° C., and preferably less than about 65° C. This is useful when the coating includes pharmaceutical or therapeutic agents that are heat sensitive, e.g. subject to chemical or physical degradation or other heat-induced negative affects, or when coating heat sensitive substrates of medical devices, e.g. subject to heat-induced compositional or structural degradation.

Depending on the particular device upon which the coatings and films of the present invention are to be applied and the particular use/result required of the device, fluorous copolymers used to prepare such devices may be crystalline, semi-crystalline or amorphous. Semi-crystalline and amorphous fluorous copolymers are advantageous where exposure to elevated temperatures is an issue, e.g. where heat-sensitive pharmaceutical or therapeutic agents are incorporated into the coatings and films, or where device design, structure and/or use preclude exposure to such elevated temperatures. Semi-crystalline fluorous copolymer elastomers comprising relatively high levels, e.g. from about 30 to about 45 weight percent of the second moiety, e.g. HFP, copolymerized with the first moiety, e.g. VDF, have the advantage of reduced coefficient of friction and self-blocking relative to amorphous fluorous copolymer elastomers. Such characteristics can be of value when processing, packaging and delivering medical devices coated with such fluorous copolymers. In addition, such fluorous copolymer elastomers comprising such relatively high content of the second moiety serves to control the solubility of certain agents, e.g. Sirolimus, in the polymer and therefore controls permeability of the agent through the matrix.

Fluorous copolymers utilized in the present inventions may be prepared by various known polymerization methods. For example, high pressure, free-radical, semi-continuous emulsion polymerization techniques such as those disclosed in *Fluoroelastomers-dependence of relaxation phenomena on composition*, POLYMER 30, 2180, 1989, by Ajroldi, et al, may be employed to prepare amorphous fluorous copolymers, some of which may be elastomers. In addition, free-radical batch emulsion polymerization techniques disclosed herein may be used to obtain polymers that are semi-crystalline, even where relatively high levels of the second moiety, e.g. greater than about 19-20 mole percent (equivalent to about 36-37 weight percent), are included.

Implantable medical devices such as stents may be coated with a film of a fluorous copolymer or polymer blend according to the present invention. Conventional stents are used in transluminal procedures such as angioplasty to restore adequate blood flow to the heart and other organs. They generally are cylindrical and perforated with passages that are slots, ovoid, circular or the like shape. Stents also may be composed of helically wound or serpentine wire structures in which the spaces between the wires form passages. Stents may be flat perforated structures that are subsequently rolled to form tubular or cylindrical structures that are woven, wrapped, drilled, etched or cut to form passages. Examples of stents that may be advantageously coated by fluorous copolymers or blends of the present invention include, but are not limited to, stents described in U.S. Pat. Nos. 4,733,665; 4,800,882; 4,886,062, 5,514,154, and 6,190,403, the contents each of which is incorporated herein in its entirety as if set forth herein. These stents can be made of biocompatible materials, including biostable and bioabsorbable materials. Suitable biocompatible metals include, but are not limited to, stainless steel, tantalum, titanium alloys (including nitinol), and cobalt alloys (including cobalt-chromium-nickel alloys). Suitable nonmetallic biocompatible materials include, but are not limited to, polyamides, polyolefins (i.e. polypropylene, polyethylene etc.), nonabsorbable polyesters (i.e. polyethylene terephthalate), and bioabsorbable aliphatic polyesters (i.e. homopolymers and copolymers of lactic acid, glycolic acid, lactide, glycolide, para-dioxanone, trimethylene carbonate, $\epsilon$-caprolactone, and blends thereof).

The biocompatible polymer coatings generally are applied to the stent in order to reduce local turbulence in blood flow through the stent, as well as adverse tissue reactions. The coatings and films formed therefrom also may be used to administer a pharmaceutically active material to the site of the stent placement. Generally, the amount of polymer coating to be applied to the stent will vary depending on, among other possible parameters, the particular fluorous copolymers and blends used to prepare the coating, the stent design, and the desired effect of the coating. Generally, the coated stent will comprise from about 0.1 to about 15 weight percent of the coating, preferably from about 0.4 to about 10 weight percent. The fluorous copolymer coatings may be applied in one or more coating steps, depending on the amount of fluorous copolymer to be applied. Different fluorous copolymers may be used for different layers in the stent coating. A diluted first coating solution can be used that comprises a fluorous copolymer as a primer to promote adhesion of a subsequent fluorous copolymer coating layer that may contain pharmaceutically active materials. The individual coatings may be prepared from different fluorous copolymers or polymer blends.

Additional coatings can be applied to delay release of the pharmaceutical agent. In addition, the polymer matrix of an additional coating can be used for the delivery of a different agent. Thus, the layering of coatings can also be employed to stage the release of the agent or to control release of different agents placed in different layers. As will be readily appreciated by those skilled in the art numerous layering approaches can be used to provide the desired drug delivery. Similarly, fluorous polymer blends may also be used to construct alternate layers of drug containing matrices.

Blends of fluorous copolymers may be used to control the release rate of different agents or to provide desirable balance of coating properties, i.e. elasticity, toughness, etc., and drug delivery characteristics, e.g. release profile. Fluorous copolymers with different solubility in solvents can be used to build up different polymer layers that may be used to deliver different drugs or to control the release profile of a drug. For example, fluorous copolymers comprising 85.5/14.5 (wt/wt) of poly(VDF/HFP) and 60.6/39.4 (wt/wt) of poly(VDF/HFP) are both soluble in DMAc. However, only the 60.6/39.4 poly(VDF/HFP) fluorous copolymer is soluble in methanol. A first layer of the 85.5/14.5 poly(VDF/HFP) fluorous copolymer comprising a drug could be over-coated with a topcoat of the 60.6/39.4 poly(VDF/HFP) fluorous copolymer made with the methanol solvent.

The coatings can be used to deliver therapeutic and pharmaceutical agents such as, but not limited to: antiproliferative/antimitotic agents including natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which don't have the capacity to synthesize their own asparagine); antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes—dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine{cladribine}); platinum coordination complexes (cisplatin, carboplatin), procarbazine, hydroxyurea, mitotane, aminoglutethimide; hormones (i.e. estrogen); Anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); antiinflammatory: such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives i.e. aspirin; para-aminophenol derivatives i.e. acetorninophen; Indole and indene acetic acids (indomethacin, sulindac, and etodolac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), azathioprine, mycophenolate mofetil); Angiogenic agents: vascular endothelial growth factor (VEGF), fibroblast growth factor (FGF); nitric oxide donors; cell cycle inhibitors; rnTOR inhibitors; growth factor signal transduction knase inhibitors; anti-sense oligonucleotide; prodrug molecules; and combinations thereof.

According to the present invention, coatings may be formulated by mixing one or more therapeutic agents with fluorous copolymers in a coating mixture. The therapeutic agent may be present as a liquid, a finely divided solid, or any other appropriate physical form. Optionally, the coating mixture may include one or more additives, e.g., nontoxic auxiliary substances such as diluents, carriers, excipients, stabilizers or the like. Other suitable additives may be formulated with the polymer and pharmaceutically active agent or compound. For example, a hydrophilic polymer may be added to a biocompatible hydrophobic coating to modify the release profile, or a hydrophobic polymer may be added to a hydrophilic coating to modify the release profile. One example would be adding a hydrophilic polymer selected from the group consisting of polyethylene oxide, polyvinyl pyrrolidone, polyethylene glycol, carboxylmethyl cellulose, and hydroxymethyl cellulose to a fluorous copolymer coating to modify the release profile.

The fluorous copolymer and pharmaceutical agent may have a common solvent. This provides a wet coating that is a true solution. In addition, coatings that contain the agent as a solid dispersion in a solution of the polymer in solvent may be employed. Under the dispersion conditions, the particle size of the dispersed powder of the agent, both the primary powder size and its aggregates and agglomerates, is small enough not to cause an irregular coating surface or to clog the slots of the stent that need to remain essentially free of coating. In cases where a dispersion is applied to the stent and the smoothness of the coating film surface requires improvement, or to be ensured that all particles of the drug are fully encapsulated in the polymer, or in cases where the release rate of the drug is to be slowed, a clear (fluorous copolymer only) topcoat of the same fluorous copolymer used to provide sustained release of the drug or another fluorous copolymer that further restricts the diffusion of the drug out of the coating can be applied.

The topcoat can be applied to a device, for example a stent, by dip coating with a mandrel to clear the matrix of the stent. This technique is commonly referred to as the dip and wipe method which is described in greater detail in U.S. Pat. No. 6,153,252, the contents of which are incorporated herein in their entirety. Other methods for applying the topcoat include spin coating and spray coating. A clear coating solution can be used that acts as a zero concentration sink and re-dissolves previously deposited drug. The time spent in the dip bath may need to be limited so that the drug is not extracted out into the drug-free bath. Drying is usually rapid so that the previously deposited drug does not completely diffuse into the topcoat.

The quantity and type of fluorous copolymers employed in the coating containing the pharmaceutical agent will vary depending on the release profile desired and the amount of drug employed. The product may contain blends of the same or different fluorous copolymers having different molecular weights to provide the desired release profile or consistency to a given formulation.

Fluorous copolymer or blend coatings may release dispersed drug by diffusion. This can result in prolonged delivery (over, 1 to 2,000 hours, preferably 2 to 800 hours) of effective amounts (say, 0.001 $\mu g/cm^2$-min to 100 $\mu g/cm^2$-min) of the drug. The dosage can be tailored to the subject being treated, the severity of the affliction, the judgment of the prescribing physician, and the like. Individual formulations of drugs and fluorous copolymers may be tested in appropriate in vitro and in vivo models to achieve the desired drug release profiles. For example, a drug could be formulated with a fluorous copolymer, or blend of fluorous copolymers, coated onto a stent and placed in an agitated or circulating fluid system, e.g. 25% ethanol in water. Samples of the circulating fluid could be taken to determine the release profile (such as by HPLC, UV analysis or use of radiotagged molecules). The release of a pharmaceutical compound from a stent coating into the interior wall of a lumen could be modeled in an appropriate animal system. The drug release profile could then be monitored by appropriate means such as, by taking samples at specific times and assaying the samples for drug concentration (using HPLC to detect drug concentration). Thrombus formation can be modeled in animal models using the $^{111}$In-platelet imaging methods described by Hanson and Harker, Proc. Natl. Acad. Sci. USA 85:3184-3188 (1988). Following this or similar procedures, those skilled in the art will be able to formulate a variety of stent coating formulations.

While not a requirement of the present invention, the coatings and films may be crosslinked once applied to the medical devices. Crosslinking may be affected by any of the known crosslinking mechanisms, such as chemical, heat or light. In addition, crosslinking initiators and promoters may be used where applicable and appropriate. In those embodiments utilizing crosslinked films comprising pharmaceutical agents, curing may affect the rate at which the drug diffuses from the coating. Crosslinked fluorous copolymers films and coatings of the present invention also may be used without drug to modify the surface of implantable medical devices.

EXAMPLES

Example 1

Use of PVDF Homopolymer and Fluorous Copolymers of Poly(VDF/HFP)

Use of a poly(VDF) homopolymer (Solef 1008 from Solvay Advanced Polymers, Houston, Tex., Tm about 175° C.) and fluorous copolymers of poly(VDF/HFP), 92/8 and 91/9 weight percent VDF/HFP, respectively, as determined by $F^{19}$NMR (e.g.: Solef 11010 and 11008, Solvay Advanced Polymers, Houston, Tex., Tm about 159° C. and 160° C., respectively) were examined as potential coatings for stents. These polymers are soluble in solvents such as, but not limited to, DMAc, N,N-dimethylformamide (DMF), dimethyl sulfoxide (DMSO), N-methylpyrrolidone (NMP), tetrahydrofuran (THF) and acetone. Polymer coatings were prepared by dissolving the polymers in acetone, at 5 weight percent as a primer, or by dissolving the polymer in 50/50 DMAc/acetone, at 30 weight percent as a topcoat. Coatings that were applied to the stents by dipping and dried at 60° C. in air for several hours, followed by 60° C. for 3 hours in a <100 mm Hg vacuum, resulted in white foamy films. As applied, these films adhered poorly to the stent and flaked off, indicating they were too brittle. When stents coated in this manner were heated above 175° C., i.e. above the melting temperature of the polymer, a clear, adherent film was formed. Such coatings require high temperatures, e.g. above the melting temperature of the polymer, to achieve high quality films.

Example 2

A Fluorous Copolymer (Solef 21508) Comprising 85.5 Weight Percent VDF Copolymerized with 14.5 Weight Percent HFP, as Determined by $F^{19}$NMR This copolymer is less crystalline than the fluorous homopolymer and copolymers described in Example 1. It also has a lower melting point reported to be about 133° C. Once again, a coating comprising about 20 weight percent of the fluorous copolymer was applied from a polymer solution in 50/50 DMAc/MEK. After drying (in air) at 60° C. for several hours, followed by 60° C. for 3 hours in a <100 mtorr Hg vacuum, clear adherent films were obtained. This eliminated the need for a high temperature heat treatment to achieve high quality films. Coatings were smoother and more adherent than those of Example 1. Some coated stents that underwent expansion show some degree of adhesion loss and "tenting" as the film pulls away from the metal. Where necessary, modification of coatings containing such copolymers may be made, e.g. by addition of plasticizers or the like to the coating compositions. Films prepared from such coatings may be used to coat stents or other medical devices, particularly where those devices are not susceptible to expansion to the degree of the stents.

The coating process in Example 1 above was repeated, this time with a coating comprising the 85.5/14.6 (wt/wt) (VDF/HFP) and about thirty (30) weight percent of rapamycin (Wyeth-Ayerst Laboratories, Philadelphia, Pa.), based on total weight of coating solids. Clear films that would occasionally crack or peel upon expansion of the coated stents resulted. Inclusion of plasticizers and the like in the coating composition will result in coatings and films for use on stents and other medical devices that are not susceptible to such cracking and peeling.

Example 3

Fluorous Copolymers Having Higher HFP Content

This series of polymers were not semi-crystalline, but rather are marketed as elastomers. One such copolymer is Fluorel FC-2261Q (from Dyneon, a 3M-Hoechst Enterprise, Oakdale, Minn.), a 60.6/39.4 (wt/wt) copolymer of VDF/HFP. Although this copolymer has a glass transition temperature (Tg) well below room temperature (Tg about-20° C.), it is not tacky at room temperature or even at 60° C. This polymer has no detectable crystallinity when measured by Differential Scanning calorimetry (DSC) or by wide angle X-ray diffraction. Films formed on stents as described above were non-tacky, clear, and expanded without incident when the stents were expanded.

The coating process in Example 1 above was repeated, this time with coatings comprising the 60.6/39.4 (wt/wt) poly (VDF/HFP) and about nine (9), thirty (30) and fifty (50) weight percent of rapamycin, based on total weight of coating solids, respectively. Coatings comprising about 9 and 30 weight percent rapamycin provided white, adherent, tough films that expanded without incident on the stent. Inclusion of 50% drug, in the same manner, resulted in some loss of adhesion upon expansion.

Changes in the co-monomer composition of the fluorous copolymer also can affect the nature of the solid-state coating, once dried. For example, the semi-crystalline copolymer, Solef 21508, containing 85.5% VDF polymerized with 14.5% by weight HFP forms homogeneous solutions with about 30% rapamycin (drug weight divided by total solids weight, e.g. drug plus copolymer) in DMAc and 50/50 DMAc/MEK. When the film is dried (60° C./16 hours followed by 60° C./3 hours in vacuum of 100 mm Hg) a clear coating, indicating a solid solution of the drug in the polymer, is obtained. Conversely, when an amorphous copolymer, Fluorel FC-2261Q, of poly(VDF/HFP) at 60.6/39.5 (wt/wt) forms a similar 30% solution of rapamycin in DMAc/MEK and is similarly dried, a white film, indicating phase separation of the drug and the polymer, is obtained. This second drug containing film is much slower to release the drug into an in vitro test solution of 25% ethanol in water than is the former clear film of crystalline Solef 21508. X-ray analysis of both films indicates that the drug is present in a non-crystalline form. Poor or very low solubility of the drug in the high HFP-containing copolymer results in slow permeation of the drug through the thin coating film. Permeability is the product of diffusion rate of the diffusing species (in this case the drug) through the film (the copolymer) and the solubility of the drug in the film.

Example 4

In Vitro Release Results of Rapamycin from Coating

Figure 2:
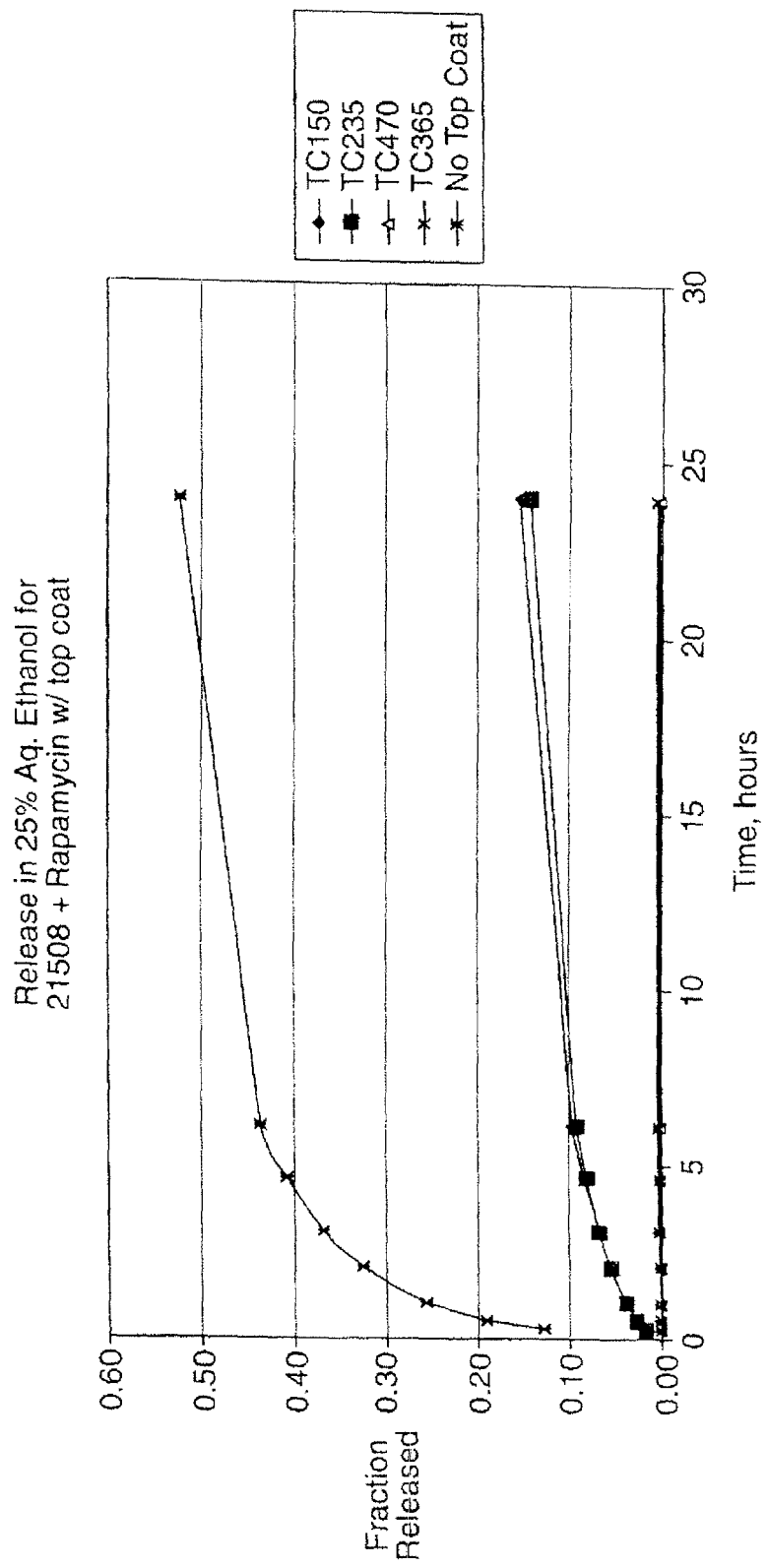
FIG. 2 illustrates the fraction of drug released as a function of time from coatings of the present invention including a topcoat disposed thereon.
Figure 3:
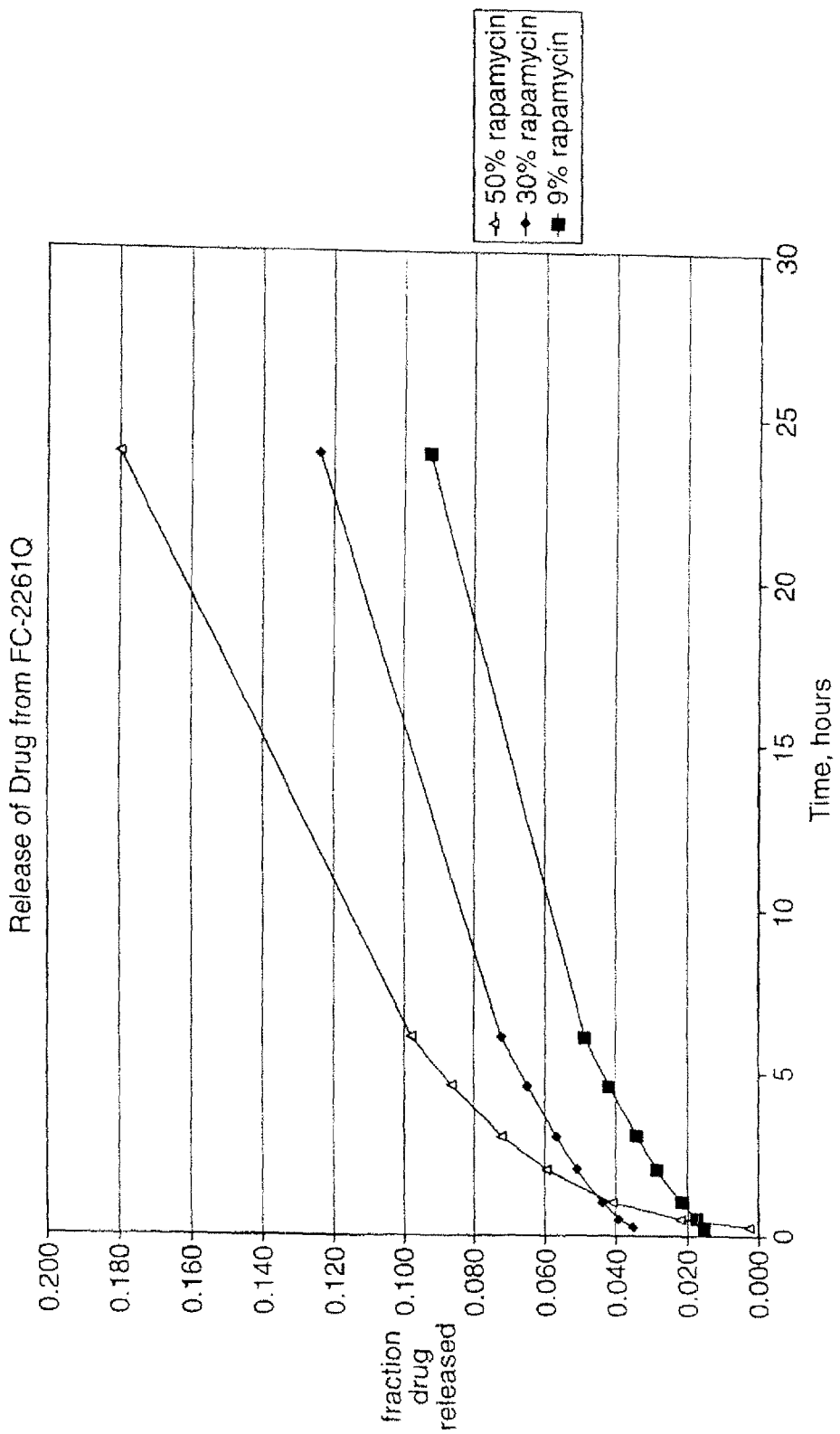
FIG. 3 illustrates the fraction of drug released as a function of time from coatings of the present invention over which no topcoat has been disposed.

FIG. 1 is a plot of data for the 85.5/14.5 VDF/HFP fluorous copolymer, indicating fraction of drug released as a function of time, with no topcoat. FIG. 2 is a plot of data for the same fluorous copolymer over which a topcoat has been disposed indicating that most effect on release rate is with a clear topcoat. As shown therein, TC150 refers to a device comprising 150 micrograms of topcoat, TC235 refers to 235 micrograms of topcoat, etc. The stents before top coating had an average of 750 micrograms of coating containing 30% rapamycin (based on drug/[drug+polymer]). FIG. 3 is a plot for the 60.6/39.4 VDF/HFP fluorous copolymer, indicating fraction of drug released as a function of time, showing significant control of release rate from the coating without the use of a topcoat. Loading of the drug in the film controls release.

Example 5

In Vivo Testing of Coated Stents in Porcine Coronary Arteries

Figure 4:
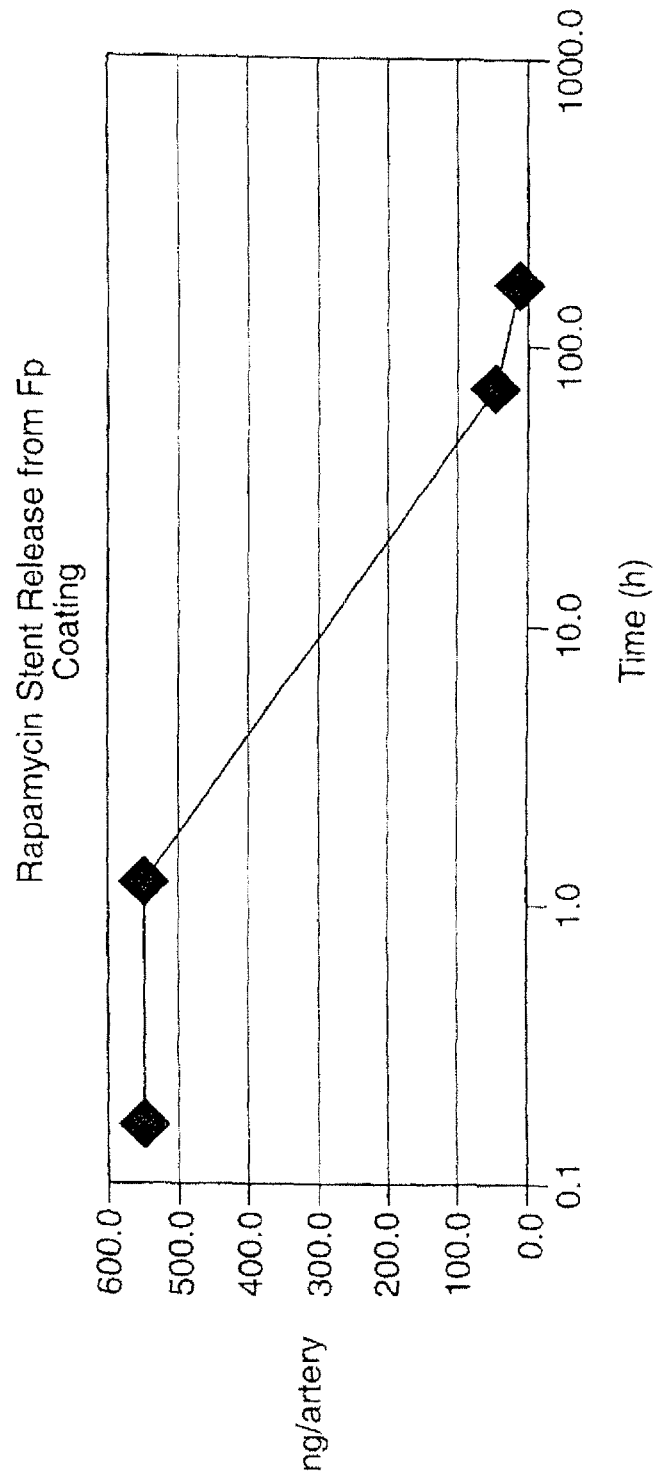
FIG. 4 illustrates in vivo stent release kinetics of rapamycin from poly(VDF/HFP).
Figure 5:
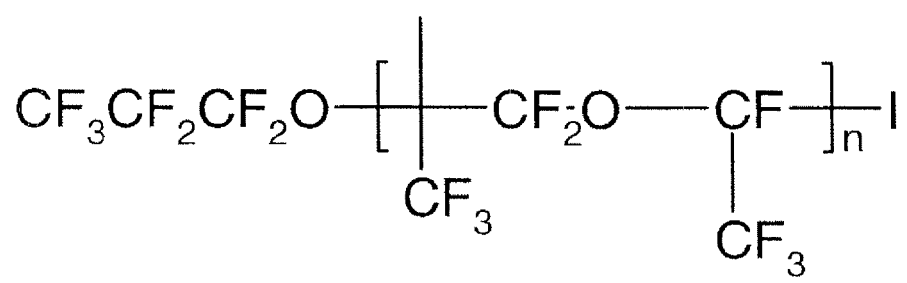
FIG. 5 shows the chemical structure of Krytox oligomer terminated with an iodine atom.

CrossFlex® stents (available from Cordis Corporation) were coated with the "as received" Fluorel FC-2261Q PVDF copolymer and with the purified fluorous copolymer of example 6, using the dip and wipe approach. The coated stents were sterilized using ethylene oxide and a standard cycle. The coated stents and bare metal stents (controls) were implanted in porcine coronary arteries, where they remained for 28 days. Angiography was performed immediately after implantation and at 28 days. Angiography indicated that the control uncoated stent exhibited about 21 percent restenosis. The fluorous copolymer "as received" exhibited about 26% restenosis (equivalent to the control) and the washed copolymer exhibited about 12.5% restenosis. Histology results reported neointimal area at 28 days to be 2.89±0.2, 3.57±0.4 and 2.75±0.3, respectively, for the bare metal control, the unpurified copolymer and the purified copolymer. The in vivo release of rapamycin from the polymer-coating matrix is shown in FIG. 4.

Example 6

Preparation of Semi-Crystalline, Poly(VDF/HFP) Copolymer Elastomers

The VDF and FIFP monomers were premixed under pressure in a pressure vessel. HPLC-grade water, surfactant and initiator were mixed outside of a 2 liter Zipperclave® reactor (Autoclave Engineers, Erie, Pa.) and then charged to the reactor, which then was sealed. The premixed monomers then were transferred under nitrogen pressure to the reactor. While stirring, the reactor was raised to the desired temperature and held for a predetermined period of time. The reactor then was cooled and residual monomer vented. The resultant polymer latex was removed from the reactor and coagulated or crashed by adding dilute hydrochloric acid, followed by aqueous sodium chloride. The resulting polymer was washed extensively with water and dried.

The fluorous copolymers then were compared with respect to kinetic coefficient of friction of a film prepared therefrom to the kinetic coefficient of friction of a film prepared from a commercial amorphous fluorous copolymer comprising 59.5 weight percent VDF copolymerized with 40.5 weight percent HFP utilizing the following procedure.

A 57.2 mm wide by 140.0 mm long polymer film was cast on a 101.6 mm wide by 203.2 mm long aluminum panel (Q-panel, anodized finish, A-48). A silicone rubber gasket was placed on the aluminum panel and clamped using binder clips. The mold was leveled in a fume hood using a bubble level. Approximate 5.0 g of 10.0% polymer solution in methyl ethyl ketone was poured into the mold slowly. The film was dried at room temperature for 3 days followed by 3 hours at 23° C. and 50% R.H. prior to testing.

The kinetic coefficient of friction of the polymer film was measured in accordance with the method described in ASTM D 1894-00, "Static and Kinetic Coefficients of Friction of Plastic Film and Sheeting", Method C. A 46.5 g Teflon block, 25.4 mm wide by 41.3 mm long by 19.1 mm thick, with an eye screw fastened in one end was used as a sled. The surface of the sled that contacted to the film was polished using 500-grit sandpaper. The Teflon sled was attached to a flexible beaded chain and pulled using an Instron tensile tester at a rate of 150 mm/min., at 23° C. and 50% R.H. Five measurements was made on each film sample. The thickness of the film was measured using a digital thickness gauge. The kinetic coefficient test results are given in Table I. The maximum kinetic coefficient of friction of five measurements of each film were averaged and reported.

The Differential Scanning calorimetry (DSC) data were obtained on the following polymers using vacuum dried films in a TA Instruments Model 2920 Modulated DSC in standard (non-modulated) DSC mode. The samples were quenched to −80° C. and heated at 10° C./min to 275° C. in nitrogen. The data are reported as ΔH (J/g) for endothermic, melting events above glass transition temperature (Tg).

Example 7

Synthesis of Grafted PVDF HFP PFPE Terpolymers

Monomers of VDF and HFP and allyl amide type perfluoropolyether were put into a pressurized reaction vessel as predetermined molar ratios. The polymerization is initiated by tert-butyl peroxide at 140° C. in perfluorohexane/acetonitrile mixture. The reaction is monitored by the decrease of pressure inside the vessel. The crude grafted polymer is precipitated in hexane yielding the final terpolymer. The reaction scheme is illustrated in below.

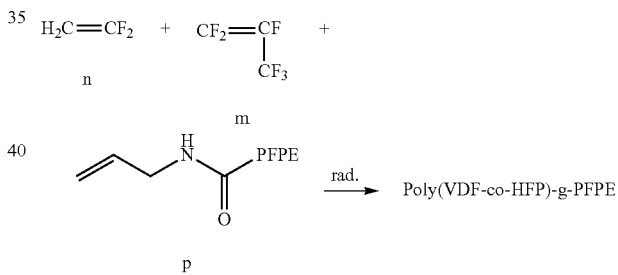

What is claimed is:

1. An implantable medical device having at least one pharmaceutical agent contained within a biocompatible coating applied to the device wherein said coating comprises a single, hydrophobic cross linked fluorous copolymer of polymerized residues of vinylidene fluoride, hexafluoropropylene, and perfluoropolyether, the copolymer having the formula P(VDF-co-HFP-co-PFPE), the coating modifying the surface of the medical device.

2. The implantable medical device of claim 1 wherein said device comprises a stent.

3. The implantable medical device of claim 1 wherein the at least one pharmaceutical agent comprises an anti-inflammatory agent.

4. The implantable medical device of claim 1 wherein the at least one pharmaceutical agent comprises an anti-restenotic agent.

5. The implantable medical device of claim 1 wherein the coating includes a therapeutic agent and an anti-thrombotic agent.

6. The implantable medical device of claim 1 wherein the molar ratio of the combined residues of VDF and HFP to perfluoropolyether is in a range from 0.95:0.05 to 0.1:0.9.

* * * * *